US006428789B1

(12) United States Patent
Strobel et al.

(10) Patent No.: US 6,428,789 B1
(45) Date of Patent: *Aug. 6, 2002

(54) RINGWORM VACCINE

(75) Inventors: Michael Strobel; Mark Werner, both of Northfield, MN (US)

(73) Assignee: Jefferson Labs, Inc., Northfield, MN (US)

( * ) Notice: Subject to any disclaimer, the term of this patent is extended or adjusted under 35 U.S.C. 154(b) by 114 days.

This patent is subject to a terminal disclaimer.

(21) Appl. No.: 09/592,417

(22) Filed: Jun. 13, 2000

Related U.S. Application Data

(62) Division of application No. 08/486,345, filed on Jun. 7, 1995, now Pat. No. 6,132,733, which is a division of application No. 07/775,912, filed on Oct. 15, 1991, now Pat. No. 5,453,273, which is a continuation of application No. 07/341,867, filed on Apr. 21, 1989, now abandoned.

(51) Int. Cl.$^7$ .......................... A61K 39/00; A01N 63/00
(52) U.S. Cl. ................ 424/184.1; 424/274.1; 424/93.5; 424/93.3; 424/93.1
(58) Field of Search .................. 424/274.1, 184.1, 424/93.3, 93.1

(56) References Cited

U.S. PATENT DOCUMENTS

| | | | |
|---|---|---|---|
| 2,011,225 A | * | 8/1935 | Krugeger |
| 3,897,550 A | * | 7/1975 | Reynolds |
| 4,368,191 A | * | 1/1983 | Sarkisov et al. |

\* cited by examiner

*Primary Examiner*—Mark Navarro
*Assistant Examiner*—Iesha Fields
(74) *Attorney, Agent, or Firm*—William, Cutler & Pickering; John W. Ryan

(57) ABSTRACT

A ringworm vaccine is disclosed comprising antigen isolated from at least one dermatophyte and a suitable carrier. The "antigen" can include a single antigen from a dermatophyte or a plurality of antigens as long as at least one antigen is included which will produce a sufficient immune response to confer resistance to ringworm infection upon the recipient of the vaccine. The antigen can also be isolated from more than one dermatophyte. If a preparation from more than one dermatophyte is made the antigen can include antigens which are common to all species of dermatophytes employed and/or antigens which are only specific to certain species. A method of producing such a ringworm vaccine is also disclosed. The method comprises making an antigen preparation comprising the dermatophyte antigen described above and combining the antigen preparation with a suitable carrier. Methods of treating a patient are also disclosed employing the vaccine of the present invention and vaccines produced according to the method of the present invention. Methods are also disclosed for treating a pregnant patient with such vaccines such that the progeny of the pregnancy exhibit resistance to ringworm infection at birth.

7 Claims, No Drawings

RINGWORM VACCINE

This application is a division of Ser. No. 08/486,345, filed Jun. 7, 1995, now U.S. Pat. No. 6,132,733 which is a division of Ser. No. 07/775,912 filed Oct. 15, 1991, now U.S. Pat. No. 5,453,273 which is a continuation of Ser. No. 07/341,867 filed Apr. 21, 1989 (abandoned).

FIELD OF THE INVENTION

The present invention relates to a vaccine containing antigens from parasitic organisms which cause ringworm, to methods of manufacturing such a vaccine and to methods of treating patients with such vaccine.

BACKGROUND OF THE INVENTION

Humans and, other mammals, including many types of domesticated animals from dairy cattle to the family cat, are plagued by ringworm (dermatomycosis) which is caused by infection by one or more of a number of parasitic fungi, generically called "dermatotphytes" (i.e., organisms which upon infection cause ringworm). Dermatophytes include without limitation the species listed in Table I.

TABLE I

Dermatophytes and Hosts

| Dermatophyte | Host(s) |
| --- | --- |
| Epidermophyton floccusum | man |
| Microsporum audouini | man (children), dogs, |
| Microsporum canis | monkeys, dogs, cats, man, sheep, monkeys, swine |
| Microsporum distortum | monkeys, dogs |
| Microsporum equinum | horses |
| Microsporum gypseum. (gypsum) | man, dogs, cats, horses |
| Microsporum nanum | swine |
| Trichophyton concentricum | man |
| Trichophyton equinum | man (children), horses |
| Trichophyton gallinae | poultry, man |
| Trichophyton gypsum (gypseum) | sheep |
| Trichophyton megnini | man, cattle |
| Trichophyton mentagrophytes | mice, rats, muskrats, chinchillas, cattle, man, horses, sheep, dogs, cats, swine, goats, rabbits, guinea pigs |
| Trichophyton quinckeanum (quinkeanum) | man, horses, sheep |
| Trichophyton rubrum | dogs, swine, foxes, primates, mice, squirrels, muskrats |
| Trichophyton schoenleini | man, cats, mice, rats, rabbits |
| Trichophyton tonsurans | man |
| Trichophyton verrucosum | cattle, man, horses, dogs, sheep |
| Trichophyton verrucosum var. album | cattle |
| Trichophyton verrucosum var. discoides | cattle, swine |
| Trichophyton verrucosum var. ochraceum | sheep |
| Trichophyton violaceum | man |

Extensive additional information relating to dermatophytes and dermatophyte mycology can be found in "The Medical Mycology Handbook" by Campbell and Stewart (John Wiley & Sons, 1980) (hereinafter the "Campbell/Stewart Handbook"), which is incorporated herein by reference as if fully set forth.

Ringworm usually manifests itself as a series of rapidly expanding, irritating lesions which can occur in any area of the skin. Dermatophytes attack chiefly keratinized tissues, particularly the stratum corneum and hair fibers resulting in autolysis of the fiber structure, breaking off of the hair and alopecia. Exudation from invaded epithelial layers, epithelial debris and fungal hyphae produce the dry crusts characteristic of the disease. The lesions progress if suitable environmental conditions for mycelial growth exist, including a warm humid atmosphere, and a slightly alkaline pH of the skin. Dermatophytes are all strict aerobes and the fungi die out under the crust in the center of most lesions leaving only the periphery active. It is this mode of growth which produces the centrifugal progression and the characteristic ring form of the lesions (hence "ring-worm"). Secondary bacterial invasion of hair follicles and other tissues is also commonly associated with ringworm infection.

Many common ailments are actually dermatophyte infections. Tinea pedis (athlete's foot or ringworm of the feet) is associated with Epidermophyton floccusum, various species of Trichophyton and, rarely, species of Microsporum and other fungi. Tinea unguium (ringworm of the nails) is caused by Trichophyton rubrum. Tinea cruris ("Jock itch" of ringworm of the groin) results from infection with Epidermophyton floccusum and species of Trichophyton. Tinea corporis (ringworm of the body) is caused by various species of Trichophyton and Microsporum, involves the smooth and hairless skin and results in either simple scaling or deep granulomas. Tinea imbricata (scaly ringworm) is a disease of the tropics and is apparently caused by a single fungus, Trichophyton concentricum. Tinea barbae (barber's itch or ringworm of the beard) is caused by various species of Trichophyton and Microsporum. Tinea capitis (ringworm of the scalp and hair) is most common in children but may affect adults. The causative organisms, various species of Trichophyton and Microsporum, may be acquired by contact with infected animals or children. Microsporum audouini is most commonly involved but Microsporum canis and Microsporum gypsum (gypseum) produce deeper, more severe lesions. Trichophyton tonsurans is also known to produce wide-spread infections in the scalp.

To date, the ringworm problem has, for the most part, been handled by post-infection treatment because an effective vaccine has not been available. The significance of skin pH in the development of ringworm is widely known. The susceptibility of humans to ringworm is much greater before puberty than afterwards when the skin pH falls from about 6.5 to about 4.0. This change is largely due to excretion of fatty acids in the sebum and these fatty acids are often highly fungistatic. For this reason, various kinds of topically-applied agents have been used to kill the infecting fungus and relieve the condition. Many treatments for ringworm are based upon alteration of skin pH by topically applying various agents (e.g., propionic acid, undecylenic acid). Other ringworm therapies have relied upon other topically applied commercially available products such as Conofite and Captan. Orally-administered agents (e.g., Griseofulvin and Ketoconazole) are also available.

Unfortunately, however, post-infection treatment cannot completely prevent in many instances. Once therapy is discontinued, reinfection usually occurs. It would therefore be desirable to provide a vaccine for ringworm to prevent infection before these adverse effects are suffered. One of the objects of the present invention is to provide such a vaccine.

SUMMARY OF THE INVENTION

In accordance with the present invention, a ringworm vaccine is disclosed comprising antigen from at least one dermatophyte and a suitable carrier. The "antigen" can include a single antigen from a dermatophyte or a plurality of antigens as long as at least one antigen is included which will produce a sufficient immune response to confer resistance to ringworm infection upon the recipient of the vaccine. The antigen can also be from more than one dermatophyte. If a preparation from more than one dermatophyte is made the antigen can include antigens which are common to all species of dermatophytes employed and/or antigens which are only specific to certain species. The antigen can be "from a dermatophyte" in that it has at least one epitope which is immunologically identical to or cross-reactive with an epitope which is found in the structure of a dermatophyte or in the structure of substances produced by the dermatophyte during infection (e.g. toxins which are produced and/or secreted by the organism during infection).

Suitable carriers for administration of vaccines are well known in the art and can include buffers, gels, microparticles, implantable solids, solvents, other adjuvants or any other means by which the antigen of the vaccine can be introduced into a patient and be made sufficiently available to produce an immune response to the antigen. In the preferred embodiments of the present invention the carrier is a lactose-containing solution of Lactated Ringers Solution (or other isotonic solution), aluminum hydroxide gel and formaldehyde. Formaldehyde is added to the preferred embodiments to serve as an agent that will kill dermatophytes and prevent contamination of non-specific fungus or bacteria. Other such agents can also be employed in formulating antigen preparations and vaccines of the present invention.

method of producing such a ringworm vaccine is also disclosed. The method comprises making an antigen preparation comprising the dermatophyte antigen described above and combining the antigen preparation with a suitable carrier. The antigen preparation can be prepared by any available means for obtaining antigen in a form which can be added to the carrier. Antigen can be isolated for use in such preparations by any available means, including without limitation homogenization of dermatophytes or portions of dermatophytes, fractionation of dermatophyte preparations, production of dermatophyte antigen by recombinant DNA technology, isolation of dermatophyte secretions and culturing of material from ringworm lesions. In the preferred embodiments of the present invention, the antigen preparation is made from homogenized cultures of appropriate dermatophytes. Preferably, all the dermatophytes in the culture are killed before the culture is homogenized (e.g., by the addition of formaldehyde or other agent which kills dermatophytes). The preferred embodiments also aspirate or filter the homogenized culture before it is added to the carrier. Finally, the antigen preparation is added to the carrier such that antigen is present in a concentration sufficient to produce an immune response and/or confer resistance upon administration of the vaccine to a patient.

Methods of treating a patient are also disclosed employing the vaccine of the present invention and vaccines produced according to the method of the present invention. Treatment can be for the purpose of producing immunity to ringworm infection (e.g., prophylactic treatment) or for the purpose of irradicating existing infection. Such patient can be a mammal of any species which is susceptible to infection by dermatophytes. Methods are also disclosed for treating a pregnant patient with such vaccines such that the progeny of the pregnancy exhibit resistance to ringworm infection at birth.

DESCRIPTION OF THE PREFERRED EMBODIMENTS

Samples of various dermatophytes are available from commercial supply houses (e.g., Difco, Gibco Cultures of *Microsporum canis, Microsporum gypsum* and *Trichophyton mentagrophytes* have also been deposited by applicants with ATCC pursuant to the Budapest treaty as accession numbers ATCC 20907, ATCC 209071, and ATCC 20972 respectively. Methods of isolating various dermatophytes are also well known to the art and can be found in the Campbell/Stewart Handbook.

The following examples are illustrative of the present invention in certain preferred embodiments. The scope of the present invention is not, however, limited to these examples and is defined by the terms of the claims appended hereto.

EXAMPLE 1

Sabouraud's Dextrose Broth ("SDB") and Sabouraud's Dextrose ("SD") plates were obtained from Difco, Gibco and DiMed (St. Paul, Minn.). SDB is a broth that contains neopeptone and bacto-dextrose in a proportion of 1:4. SD agar contains neopeptone, bacto-dextrose and agar in proportions of 2:8:3. SDB and SD agar for plates can also be prepared according to the recipes found on pages 384–85 of the Campbell/Stewart Handbook.

Separate samples of *Microsporum canis, Microsporum gypsum* and Alternaria sp. (a fungus which does not cause ringworm) were isolated from a human (who had been infected by an infected cat), cattle and cattle, respectively, as follows: A ringworm lesion containing the desired fungus was washed with 70% alcohol solution and allowed to air dry. The surface of the lesion was then scraped with a scalpel to remove some of the infected tissue. The scrapings were then placed in SDB and cultured. After significant growth was observed, a sample from each culture was plated on SD plates to check the purity of the culture. Pure cultures were then used as inocula as described below.

*Microsporum canis, Microsporum gypsum* and Alternaria sp. were each used to inoculate a separate 10 ml vial containing SDB. The three vials were then incubated at room temperature for 4 days. Each vial was shaken vigorously once during each day of culture.

The contents of each vial was then added to a separate ordinary 400 ml growth chamber (commercially available from Corning) containing 90 ml SDB. The chambers were then grown at room temperature until maximum growth (i.e., no increase from previous day measured by eye) was reached. The chambers were shaken vigorously once during each day of culture. When maximum growth was reached, a sample from each chamber was plated onto SD plates to check the purity of the cultures. Maximum growth for *Microsporum canis, Microsporum gypsum* and Alternaria sp. was found to be approximately 4 days, 7 days and 4 days, respectively.

Once the cultures were determined to be pure, formaldehyde diluted with Lactated Ringers Solution was added to each chamber such that the final concentration of formaldehyde in each chamber was 0.2% in a total volume of 400 ml. The cultures were then allowed to sit for 4 days. Cultures were plated onto SD plates to see if all fungi had been killed.

Once all fungi were killed, cultures of *Microsporum canis, Microsporum gypsum* and Alternaria sp. were separately homogenized using an Oster blender for 2–5 minutes on a low setting, taking care such that the blender did not overheat and heat the homogenized cultures. The homogenized cultures were then allowed to stand for approximately 48 hours.

Each homogenized culture was then aspirated through a Whatman 4 filter. The aspirates from all three organisms were then combined. 72 ml of aluminum hydroxide/methylcellulose gel (commercially available from Barre) or equivalent was added as a standard adjuvant and the mixture was brought up to a final volume of 3600 ml with Lactated Ringers Solution to produce the final vaccine.

5 ml of the final vaccine was administered to cattle on several farms. Depending on the farm, 50–100% of the cattle treated were cured of preexisting ringworm infection and exhibited resistance to reinfection after treatment. Those infections not succumbing to treatment with the vaccine were probably caused by infecting organisms not included in the vaccine (i.e., other than *Microsporum canis* or *Microsporum gypsum*).

1 ml of the final vaccine was also administered to cats. The cats treated exhibited resistance to ringworm infection up to 18 months after administration of the vaccine.

EXAMPLE 2

A vaccine was prepared from *Microsporum canis, Microsporum gypsum* and *Trichophyton mentagrophytes* using the procedure described in Example 1.

5 ml of the final vaccine was administered to cattle. As of the filing date of this application, all cattle treated have exhibited continued resistance to ringworm infection for a period of up to 7 months.

EXAMPLE 3

A sample of *Microsporum canis* was isolated as described in Example 1. The sample was then used to inoculate a 10 ml vial containing SDB. The vial was incubated for 4 days at 95° F., shaking the vial vigorously once during each day of culturing.

The contents of the vial was then added to a growth chamber containing 90 ml SDB. The growth chamber was incubated until maximum growth was reached at 95° F, shaking the chamber vigorously once during each day of culturing. When maximum growth was reached (approximately 4 days), a sample from the chamber was plated onto SD plates to check the purity of the culture.

Once the culture was determined to be pure, formaldehyde diluted with Lactated Ringers Solution was added to the chamber such that the final concentration of formaldehyde in the chamber was 0.2% in a total volume of 400 ml. The culture was then allowed to sit for 4 days. The culture was plated onto SD plates to see if all fungi had been killed.

Once all fungi were killed, the culture was homogenized using an Oster blender for 5 minutes on a low setting, taking care such that the blender did not overheat and heat the homogenized culture. The homogenized cultures were then allowed to stand for approximately 48 hours.

The homogenized culture was then aspirated through a Whatman 4 filter. Formaldehyde, aluminum hydroxide gel and Lactated Ringers Solution were added to the homogenized culture such that the final concentration of formaldehyde and aluminum hydroxide gel in a total volume of 3000–4000 ml was 0.2% and 2% respectively. This solution was the final vaccine.

Cats were treated with the final vaccine in varying doses depending on the age of the cat. Adult cats received 1 ml, 5–7 week kittens received 0.25 ml and 9 week kittens received 0.5 ml. Approximately 95% of the cats treated exhibited resistance to ringworm infection for (as of the filing of this application) up to 8 months. Administration of this final vaccine to a pregnant cat was also observed to confer resistance to infection upon the progeny of the pregnancy for a period of approximately 4–5 weeks. No adverse effects were observed with respect to the pregnancy or the progeny.

EXAMPLE 4

Four homogenized and aspirated cultures were prepared from *Microsporum canis, Microsporum gypsum* and *Trichophyton mentagrophytes* according to the procedure described in Example 3. The aspirates were then combined with each other and with formaldehyde, aluminum hydroxide gel and Lactated Ringers Solution such that the final concentration of formaldehyde and aluminum hydroxide gel in a total volume of 4000 ml was 0.2% and 2%, respectively. This solution was the final vaccine.

5 ml was administered to cattle. All cattle treated exhibited resistance to ringworm infection for (as of the filing of this application) up to 8 months.

From the foregoing, it will be obvious to those skilled in the art that various modifications in the above-described methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method comprising the administration of a ringworm vaccine to a domesticated animal for the purpose of producing immunity to ringworm infection, said ringworm vaccine comprising an effective amount of a homogenized, chemical agent-killed pure *Microsporum canis* culture provided in a carrier.

2. The method of claim 1, wherein the vaccine comprises an effective amount of both homogenized, chemical agent-killed pure *Microsporum canis* and homogenized, chemical agent-killed pure *Microsporum gypsum.*

3. The method of claim 1, wherein the vaccine comprises an effective amount of a combination of homogenized, chemical agent-killed pure *Microsporum canis*, and homogenized, chemical agent-killed pure *Trichophyton mentagrophytes.*

4. The method of claim 1, wherein the vaccine comprises an effective amount of a combination of homogenized chemical agent-killed pure *Microsporum canis*, homogenized, chemical agent-killed pure *Microsporum gypsum*, and homogenized, chemical agent-killed pure *Trichophyton mentagrophytes.*

5. A method comprising the administration of a ringworm vaccine to a domesticated animal for the purpose of eradicating existing dermatophyte infection, said ringworm vaccine comprising an effective amount of a homogenized, chemical agent-killed pure *Microsporum canis* culture provided in a carrier.

6. The method of claim 5 wherein the domesticated animal is a cat.

7. A method comprising the administration of a ringworm vaccine to a pregnant cat for the purpose of conferring resistance to a dermatomycosis in the offspring of said pregnant cat, said ringworm vaccine comprising an effective amount of homogenized, chemical-agent killed pure *Microsporum canis* culture provided in a carrier.

* * * * *